United States Patent [19]

Burzynski

[11] 4,444,890

[45] Apr. 24, 1984

[54] TESTING PROCEDURE TO AID DIAGNOSIS OF CANCER AND EVALUATE THE PROGRESS OF CANCER THERAPY

[76] Inventor: Stanislaw R. Burzynski, #5 Concord Cir., Houston, Tex. 77024

[21] Appl. No.: 346,291

[22] Filed: Feb. 5, 1982

[51] Int. Cl.³ .............................................. G01N 33/68
[52] U.S. Cl. ........................................ 436/64; 436/86; 436/89
[58] Field of Search ............................. 436/64, 86–90, 436/63

[56] References Cited

U.S. PATENT DOCUMENTS 4,270,924 6/1981 Crooke et al. ......................... 436/64

OTHER PUBLICATIONS

Burzynski et al., "Antneoplaston A in Cancer Therapy(I)", Physiol. Chem. & Physics, 9:485–500(1977).
Burzynski, "Antineoplastons: Biochemical Defense Against Cancer", Physiol. Chem. & Physics, 8:275–279 (1976).
Beall et al., "Polypeptides that Inhibit Human Breast Cancer Cell Division", Cancer Biochem. Biophys., 3:93–96(1979).
Burzynski et al., "Antineoplastic Peptides from Urine and Their Inhibition of DNA, RNA, and Their Proteins", No. 183, May 1976, Special Listing of Current Cancer Research on Mechanism of Action of Anticancer Agents.
Sadee et al., Chemical Abstracts, vol. 85, 1976, No. 85:71930u.
Mardasher et al., Soviet Medicine 31(3): 27–30 (Mar. 1978).
Gross et al., Physiol. Chem. & Phys. 8: 161–166 (1976).

Primary Examiner—Arnold Turk
Attorney, Agent, or Firm—Arnold, White & Durkee

[57] ABSTRACT

Antineoplastons are termed a group of plasma, tissue and urinary peptides and amino acid derivatives capable of modulating abnormal tissue growth, such as neoplastic disease. Antineoplastons, when administered to persons with neoplastic disease, have been shown to be effective against several forms of cancer and tumors. A procedure is provided herein for the determination of antineoplaston levels in physiological tissues or fluids, especially plasma and urine. The procedure involves purification of antineoplastons by high performance liquid chromatography on silica gel followed by resolution of antineoplastons by high performance liquid chromatography on sulfonated polystyrene. A quantitative determination of antineoplaston tissue or fluid levels provides valuable data to aid clinical diagnosis of cancer. In addition, the quantitative determination also provides a means for monitoring the efficacy of antineoplastic therapy.

47 Claims, 1 Drawing Figure

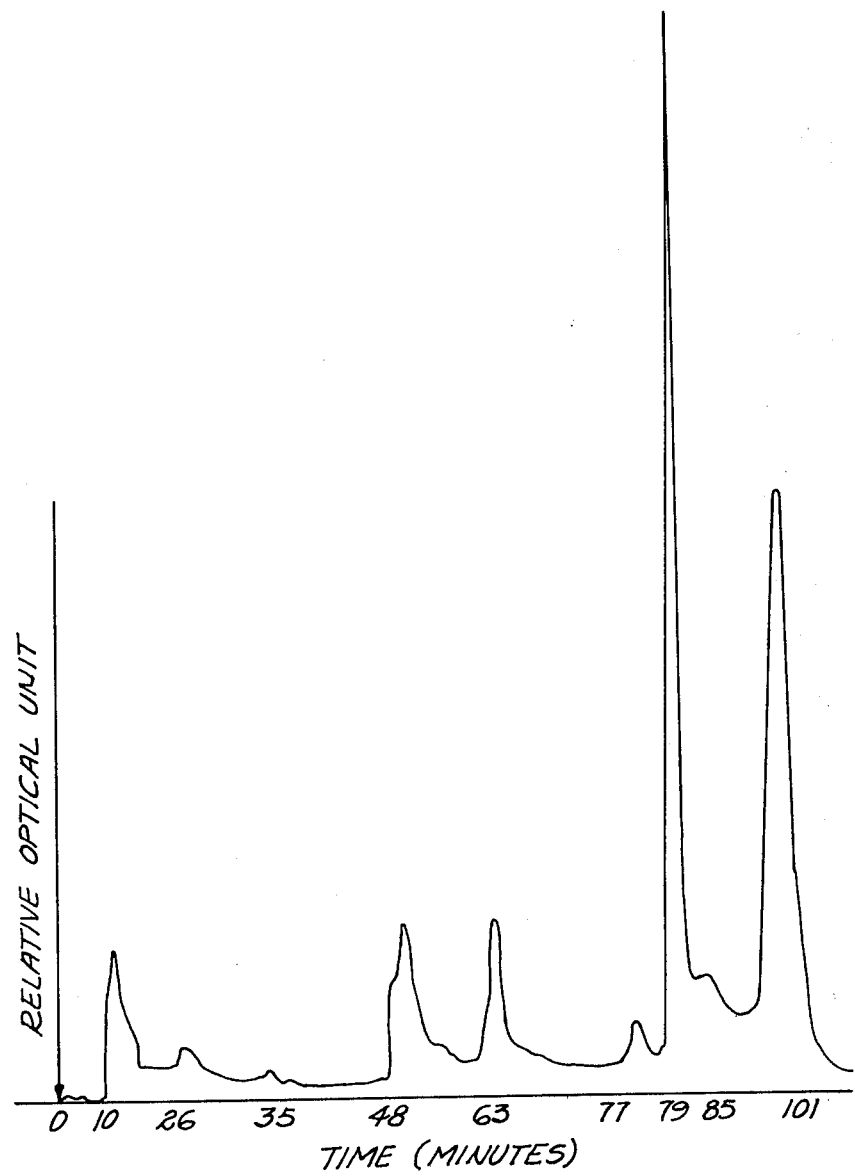

TESTING PROCEDURE TO AID DIAGNOSIS OF CANCER AND EVALUATE THE PROGRESS OF CANCER THERAPY

BACKGROUND OF THE INVENTION

The present invention relates generally to bioanalytical testing procedures to aid in the diagnosis of cancer and to evaluate therapeutic treatment by antineoplastons. More particularly, the invention relates to a quantitative determination of antineoplaston levels in physiological tissues, particularly plasma and urine.

Investigations into the presence of physiologically or pathologically active peptides in various physiological tissues have been ongoing for the past 80 years. Biologically active polypeptides have been isolated from mammalian urine which have demonstrated hormone-like activity or regulation of biological function. Examples of biologically active polypeptide compositions isolated from urine include growth factors, pituitary hormones, and kinins.

The practically infinite variety of peptides that can be formed by the combination of the twenty common amino acids has prompted many investigators to suggest that peptides may constitute a system carrying information from cell to cell and organ to organ. Following this view on the regulatory significance of peptides, researchers have isolated urinary peptides which exert an influence on blood pressure, behavior modification, cardiovascular regulation, and smooth muscle activity.

Accordingly, it has been considered by a number of researchers that neoplastic growth may be controlled by naturally occurring biochemical defense mechanisms. The immunological process has most often been attributed with antineoplastic activity (see for example, Aoki et al, *Prog. Exp. Tumor Res.*, 19:23, 1974). There are however, other possible mechanisms.

It has been suggested that neoplasia is a disease of cell differentiation. Given the large number of differentiating cells and assuming the possibility of error in the program for differentiation, groups of abnormally growing cells can often arise under the influence of carcinogenic factors. Without a reliable mechanism for "normalizing" such erroneously developed cells, the organisms would not live very long. Such a mechanism should be able to correct the growth of newly developed neoplastic cells and direct them into normal differentiation pathways. It is Applicant's belief that peptides are ideal compounds to function as information-carrying molecules regulating cell differentiation.

In recent years, Applicant has described a number of medium-sized peptides derived from human urine, which demonstrate inhibition of DNA synthesis and mitosis in cultures of various neoplastic cells without significant inhibition of normal cell replication [see Burzynski, *Physiol. Chem. Phys.*, 5:437 (1973); Burzynski et al, *Fed. Proc.*, 32:766 (1973); Burzynski et al, *Physiol. Chem. Phys.* 8:13 (1976); Burzynski et al, *Fed. Proc.* 35:623 (1976); Gross et al, *Physiol. Chem. Phys.*, 8:161 (1976); Gross et al, *Clin. Chem.* 23:148 (1977); Burzynski, *Physiol. Chem. Phys.*, 8:275 (1976); and Burzynski et al, *Physiol. Chem. Phys.* 9:485 (1977)]. More recently, Applicant has purified, isolated and characterized certain low molecular weight peptide fractions, peptides and amino acid derivatives isolated from urine which exhibit impressive antineoplastic activity [see U.S. patent application Ser. No. 279,728, filed July 2, 1981, entitled "Purified Antineoplaston Fractions and Methods of Treating Neoplastic Disease" and copending application, Ser. No. 330,383 filed Dec. 15, 1981, a continuation-in-part application of the above-referenced application Ser. No. 279,728].

The active compounds, but heretofore unidentified discrete compounds, from these fractions have been given the working name "antineoplastons". Applicant has defined antineoplastons as substances produced by a living organism that protect it against development of neoplastic growth by a nonimmunological process and that do not significantly inhibit the growth of normal tissues. In particular, Applicant has elucidated antineoplastons which are chemically classified as peptides, amino acid derivatives or hydrolysis products thereof, although he makes no representations that antineoplastons are restricted to this chemical class.

Applicant has demonstrated through extensive clinical evaluation that the antineoplaston fractions and peptides referenced above are useful in the treatment of human neoplastic disease. To date, Applicant has established a complete remission rate of about 45% and overall improvement in 93% of patients with advanced malignant neoplastic disease treated with antineoplaston fraction A2.

According to Applicant, antineoplastons, in general, offer a unique biological mechanism to combat cancer. The mechanism is viewed as a repair of young or developing cancer cells to reinstitute a more normal way of development. Research on the part of the Applicant has indicated that antineoplastons are present in the tissues and body fluids of healthy people, while people with cancer exhibit an aberrant concentration of antineoplaston for any given tissue relative to the concentration associated with healthy persons. Consequently, it is reasoned by Applicant, that the antineoplastons offer a defense or metabolic correction mechanism to protect individuals from the thousands of carcinogenic factors present in the environment which can trigger the growth of cancer.

SUMMARY OF THE INVENTION

In accordance with the present invention, a bioanalytical testing procedure is provided which is useful as an aid to diagnose neoplastic disease in a subject suspected of having neoplastic disease. Neoplastic disease in the context of the present invention is applied in its conventional usage to include any abnormal mass of tissue that grows by cellular proliferation more rapidly than normal and continues to grow after the stimuli for new growth has ceased. Neoplastic disease encompasses both benign and malignant tumors and leukemias.

Generally in accordance with the present invention, a tissue or fluid sample is first obtained from the tested subject. This physiological specimen is then analyzed to determine the level of antineoplaston present within the sample. The level of antineoplaston of the test sample is compared to a standard antineoplaston level established for the same tissue or fluid of a healthy, normal subject unaffected by neoplastic disease. A significant difference in antineoplaston levels is indicative of the presence of neoplastic disease.

The term "antineoplaston" as used herein defines substances produced by a living organism that protect it against the development of neoplastic growth by a nonimmunological process, and that do not significantly inhibit the growth of normal tissue. Antineoplaston offers a selective, endogenous regulatory control of neoplastic tissue proliferation. According to Applicant, organisms which exhibit aberrant levels of endogenous antineoplaston are susceptible to neoplastic disease.

In accordance with preferred embodiments of this invention, the antineoplaston levels evaluated are those antineoplastons which are characterized as peptides and amino acid derivatives; and, in particular, small-sized peptides having less than ten amino acid residues. An especially desired antineoplaston indicator level is that substantially homogeneous antineoplaston fraction which contains the peptide 3-[N-phenylacetylaminopiperidine]-2, 6-dion.

The implementation of the methods of the present invention, however, is not limited to antineoplastons which are characterized as peptides. The procedures of this invention encompass the assessment and correlation of other antineoplaston substances as they become identified.

The physiological test samples obtained from subjects are suitably organ biopsy samples, spinal fluid, whole blood, plasma, serum, lymph, urine, saliva, mucus, connective tissue and feces. For purposes of convenience and satisfaction of instrument sensitivity specifications, Applicant prefers to assess antineoplaston levels from urine, whole blood, plasma or serum.

According to preferred embodiments, antineoplaston is first extracted from test samples and then fractionated by chromatographic processes into discrete fractions of substantially homogenous antineoplaston composition. The antineoplaston levels of selected fractions are then evaluated and compared to standards.

In an alternative embodiment of the invention, antineoplaston levels are evaluated from two different physiological sources, preferably urine and a blood component such as plasma, serum or whole blood. The ratio of the two values is then compared to a standard ratio established for like samples obtained from normal healthy subjects unaffected by neoplastic disease. A significant difference in the two ratios is indicative of the presence of neoplastic disease.

Another application of the present invention is the assessment of neoplastic regression in a subject undergoing antineoplastic therapy, in particular, either conventional chemotherapy or antineoplaston therapeutic administration. In monitoring the subject, regression of neoplastic disease is indicated by antineoplaston levels which substantially approach normal values.

As used herein the terms "significant difference" and "substantially the same value" are relative terms construed according to recognized statistical sampling methods.

BRIEF DESCRIPTION OF THE DRAWING

The FIGURE represents a typical spectrograph profile of antineoplaston components elaborated by chromatographic fractionation.

DETAILED DESCRIPTION OF PREFERRED EMBODIMENTS

The present invention will be described in terms of preferred embodiments known to the Applicant at the time of this application which represent the best mode corresponding to the quantitative determination of antineoplaston levels in biological tissues and correlation of said levels to aid in the diagnosis of neoplastic disease and evaluate the therapeutic treatment of administered antineoplastons.

In accordance with such preferred embodiments, antineoplaston levels are determined for a selected biological tissue or body fluid. Preferably suited as sample fluids for the testing procedure are serum, plasma or urine, since these physiological fluids are conveniently obtainable for any given diagnostic or clinical assay. Furthermore, plasma and urine typically have demonstrated an even distribution of antineoplastons throughout the fluid sample. Suitably, however, antineoplaston levels from solid tissues such as those tissues extracted as part of a biopsy study can be evaluated and implemented into the correlation schemes of this invention. It will be appreciated, of course, by clinicians and diagnosticians that plasma, serum, whole blood, or urine samples provide the most convenient, reliable, inexpensive, and safe sources for evaluation and determination of antineoplaston levels.

Collection of tissue or fluid samples are carried out as would be provided for by the typical clinical assay. No special collection mechanism need be employed. Furthermore, the collected tissue or fluid can be stored under standard refrigeration conditions for several days without significant impairment of the analytical assay sensitivity. Of course, as with most clinical assays, testing performed on fresh samples is most often reliable and accurate.

The amount of sample taken from a tested subject will vary with the tissue or fluid to be evaluated and the sensitivity of the analytical equipment employed. These factors are better illustrated by the examples which follow. Any adjustments necessary to suit specific analytical instrumentation will be within the technical skill of the practitioners in the art.

Applicant prefers for purposes of the present invention to evaluate the antineoplastons characterized as small-sized peptides having less than 10 amino acid units, and fully describes them in his copending U.S. patent application Ser. Nos. 279,728 and 330,383, the disclosures of which are hereby incorporated by reference. Suitably, however, the testing methods of this invention can be applied to the other antineoplastons such as the medium-sized peptides described in the many articles authored by the Applicant and listed in the background section. Furthermore, as other antineoplaston compounds are isolated, recognized or classified, the techniques of this invention are contemplated to encompass their evaluation and implementation into the correlation scheme to aid in the diagnosis of cancer and evaluate therapeutic treatment by antineoplastons.

Once the particular tissue or fluid sample has been evaluated for a predetermined antineoplaston, this value is compared to a normal standard value, a standard ascribed by a statistically revelant average obtained from like tissue or fluid antineoplaston levels evaluated from a population of normal, healthy, non-cancerbearing subjects.

Although a single tissue or fluid evaluation for antineoplaston is sufficient for the purposes of this invention to correlate abnormal versus normal values of antineoplaston, it is, of course, preferable to determine antineoplaston levels for at least two different tissue or fluid components. For example, it is most preferable that antineoplaston levels be evaluated from both the plasma and urine. A ratio of these values provides an extremely sensitive indicator value for correlation purposes. This becomes readily apparent when one considers that the two compartments, plasma and urine are the predominant fluid components of the body. Therefore, in the normal course of events, at steady state conditions, those substances that are rapidly cleared from the plasma will typically concentrate in the urine, and the converse is usually true for those substances that are slowly cleared from the body. Thus, a ratio of values taken from complementary compartments provides a value which is more reliable and sensitive than either single compartmental value taken alone.

A. Purification of Antineoplastons from Plasma and Urine

In the examples which follow, a small-sized antineoplaston fraction was purified from both urine and plasma of normal subjects and patients known to have cancer.

In accordance with preferred methods of this invention, 4 to 8 ml of blood were withdrawn from the vein of normal persons or cancer patients and collected in the presence of 50 units of heparin. The whole blood was centrifuged to remove blood cells and particulate materials. The plasma thus obtained was mixed with 5 volumes of absolute ethanol, and the resultant precipitate was separated by centrifugation and discarded. Next, the ethanol supernatant was evaporated to dryness by freeze drying. To remove insoluble particulate material, the residue was dissolved in 0.5 M acetic acid (twice the volume of blood specimen originally obtained), and filtered through a Millipore membrane having an average pore size of $0.45\mu$.

The small-sized antineoplastons present in the redissolved residue solution were purified by high performance liquid chromatography, using, in this instance, a Waters Prep LC system, equipped with a Prep 500 C-18 silica gel cartridge column (bonded phase type silica gel). The column was successively washed with 0.5 M acetic acid and water to remove basic compounds and hydrophilic materials, including salts and amino acids. The adsorbed antineoplastons were afterwards eluted from the column with methanol. Methanol was removed by freeze drying. As a further clean-up, the antineoplaston residue was dissolved in 0.2 milliliters of water per milliliter of plasma and filtered through a Millipore membrane having an average pore size of $0.45\mu$ to remove insoluble materials.

Urine specimens were treated similarly, but without going through ethanol precipitation. 10 ml of urine, preferably from 24-hour pooled specimens, were adjusted to pH 2.5 with 0.5 M acetic acid, and filtered through a Millipore membrane having an average pore size of $0.45\mu$. To purify the antineoplastons, the filtrate was passed through a column of C18 as above described. The resulting antineoplaston residue was dissolved in 2 ml of water and filtered through a Millipore membrane having an average pore size of $0.45\mu$ to remove insoluble matter.

Alternatively, antineoplaston preparations can be purified from urine or plasma utilizing the preparative schemes provided for in the isolation and purification of antineoplaston fractions A1-A5 described in Applicant's copending U.S. patent application Ser. Nos. 279,728 and 330,383, the disclosures of which are hereby incorporated by reference. [See Sections A-E therein].

B. Resolution and Quantitative Determination of Antineoplastons

A predetermined aliquot of plasma (0.1 ml) or urinary (0.1 ml) antineoplaston preparation was injected into a column of sulfonated polystyrene, 0.325 cm×30 cm, equilibrated with Dionex Pico-Buffer Solution A, pH 3.25, obtained from Pierce Chemical Co., Rockford, Ill., 61105. The column was equipped with a surrounding water jacket for temperature control. The elution was commenced by the equilibration buffer solution at 46° C. for 23 min., followed by Dionex Pico-Buffer B, pH 3.80 at 70° C. for 15 min., and finally by Buffer Solution C, pH 4.10, at 70° C. for 60 min. The flow rate was kept at 0.2 ml per minute. A pressure of 400 psi was necessary to maintain this flow rate. The changes of buffer solutions and temperature were automatically controlled by a computer programmed system.

The eluant as it came off the column was pumped into a reaction coil to merge with a stream of ninhydrin solution [2% (w/v) in 4 M sodium acetate, pH 5.51: methoxyethanol 1:3] at a flow rate of 0.1 ml per min., the reaction taking place at 110° C. The reacted color product was then split into two streams, each stream passing through a double-beam spectrophotometer for the detection of absorbance, respectively at 570 m$\mu$ and 440 m$\mu$. The absorption peaks were automatically recorded and integrated by Hewlett Packard integrator, Model No. 3390A. The integrated data was converted into equivalent amounts of $\alpha$-amino group, using standard amino acids as reference. Under the conditions described above, standard amino acids were resolved according to the retention times presented in Table I. The average absorption at 570 m$\mu$ was 0.058 optical unit per nmole.

TABLE 1

| Standard Retention Times of Amino Acids | |
|---|---|
| Amino Acids | Retention Times (minutes) |
| Aspartic acid | 18.0 |
| Threonine | 21.5 |
| Serine | 22.7 |
| Glutamic acid | 26.0 |
| Proline | 30.0 |
| Glycine | 38.4 |
| Alanine | 38.9 |
| Cysteine | 42.0 |
| Valine | 47.0 |
| Methionine | 49.0 |
| Isoleucine | 52.2 |
| Leucine | 53.8 |
| Tyrosine | 59.2 |
| Phenylalanine | 64.0 |
| Lysine | 72.0 |
| Ammonia | 78.0 |
| Histidine | 80.2 |
| Arginine | 93.5 |

Antineoplaston components are characterized by the retention times, and named accordingly. For example, if an antineoplaston component takes 60 minutes to be eluted, it is called AC60 (Antineoplaston Component-60). A typical profile of antineoplaston components is shown in the FIGURE. Peaks are identified as AC 10, AC 26, AC 35, AC 48, AC 63, AC 79, AC 85 and AC 101.

AC 79 is the major component of human antineoplastons. It is also the component best characterized in terms of chemistry and antitumor activity. The main component of this peak was identified as 3-[N-phenylacetylaminopiperidine]-2, 6-dion. Both the synthetic product and the natural compound purified from urine have been shown to inhibit macromolecular synthesis, including DNA synthesis and cell replication, of cultured human breast cancer cells. The other components have not at present been well characterized. AC 10 is a collection of many acidic compounds passing through the column unadsorbed. AC 48, AC 63 and AC 101 comprise, like AC 79, peptides or amino acid derivatives. Although the chemical nature of these various components have not been identified, these components are amenable to evaluation according to the methods of this invention for the diagnosis and evaluation of cancer patients.

Data associated with plasma and urinary antineoplaston levels of normal persons are summarized in Table 2. AC 10, AC 26, AC 48, AC 63 and AC 101 are detectable in most normal persons; whereas, AC 35, AC 85 and AC 93, frequently detected in cancer patients, are either absent or present in small quantities in normal persons. It seems that under normal circumstances, AC 79 and AC 10 are retained in the plasma while AC 26, AC 48, AC 63 and AC 101 are preferentially excreted in the urine.

TABLE 2

Standard Control Antineoplaston Values for Normal, Healthy Subjects

| Antineoplaston Component | Plasma nMole/ml | Urine nMole/ml | Plasma Urine | Urine [24 hr.] μMole/day | Plasma $\times 10^3$ [24 hr.] |
|---|---|---|---|---|---|
| 10 | 3.3 | 3.1 | 1.06 | 3.2 | 1.03 |
| 26 | 6.6 | 7.7 | 0.86 | 10.1 | 0.65 |
| 48 | 4.3 | 11.4 | 0.38 | 13.0 | 0.33 |
| 63 | 7.2 | 18.3 | 0.39 | 17.8 | 0.41 |
| 79 | 61.8 (32–110) | 57.7 (31–87) | 1.07 | 64.4 (44–77) | 0.96 |
| 101 | 9.5 | 23.8 | 0.40 | 27.4 | 0.35 |

Plasma values are averaged over 24 persons (twelve male and twelve female). Urine values are averaged over 14 persons (seven male and seven female). The 24 hour pooled urine value is the average taken of six persons (three male and three female). The values within parenthesis given for AC 79 indicate normal ranges.

C. Plasma and Urine Levels of AC 79 in Cancer Patients

The results of antineoplaston urine and plasma analyses of 92 confirmed cancer patients are listed in Tables 3–7. Patients' data is classified, according to plasma and urinary levels of AC 79, into 5 categories presented in Tables 3–7. A plasma below 40 nmoles/ml is classified as a low plasma level and above 40 nmoles/ml as a normal level. Urinary excretion above 80 μmoles/day is classified as a high urinary level, between 40 to 80 μmoles/day as a normal urinary level, and below 40 μmoles/day as a low urinary level. With this classification, 50.5% of the patients tested belong to low plasma and high urinary levels, 18.7% belong to low plasma and normal urinary levels, 13.2% belong to low plasma and low urinary levels, 12.1% belong to normal plasma and high urinary levels and 5.5% belong to normal plasma and normal urinary levels. Thus, a total of 82.4% shows a deficiency of AC 79 in the plasma.

It appears that deficiency of AC 79 is a characteristic abnormality exhibited by cancer patients. Since the AC 79 fraction is capable of suppressing the growth of cancer cells tested in vitro [see Applicant's copending applications, Ser. Nos. 279,728 and 330,383], it is conceivable that a deficiency of AC 79 in the plasma is an important factor associated with malignancy.

Results presented in Tables 3 through 7 also reveal that a vast majority of cancer patients, approximately 90%, show a plasma/urine ratio of AC 79 that is significantly lower than a normal control ratio. Thus, excessive excretion of AC 79 may be another characteristic abnormality of cancer patients.

TABLE 3

Patients with Low Plasma Level and High Urinary Excretion of AC 79

| Patient Test Number | Plasma Level (nMoles/ml) | Urinary Excretion (μMoles/day) | Plasma $\times 10^3$ Urine [24 hr.] |
|---|---|---|---|
| 365 | 14.6 | 84.0 | 0.17 |
| 148 | 20.3 | 249.5 | 0.08 |
| 225 | 31.9 | 97.9 | 0.32 |
| 133 | 10.3 | 168.0 | 0.06 |
| 64 | 4.8 | 95.4 | 0.05 |
| 283 | 23.2 | 167.1 | 0.14 |
| 342 | 6.8 | 138.5 | 0.03 |
| 237 | 6.9 | 92.2 | 0.07 |
| 242 | 23.0 | 289.0 | 0.08 |
| 240 | 20.2 | 182.2 | 0.11 |
| 150 | 39.4 | 255.0 | 0.15 |
| 276 | 15.8 | 145.4 | 0.11 |
| 110 | 18.9 | 133.0 | 0.14 |
| 112 | 14.2 | 326.0 | 0.01 |
| 182 | 32.0 | 304.0 | 0.11 |
| 114 | 14.8 | 580.0 | 0.02 |
| 111 | 6.7 | 84.8 | 0.08 |
| 119 | 31.2 | 239.3 | 0.13 |
| 322 | 13.8 | 165.9 | 0.08 |
| 158 | 18.6 | 174.0 | 0.11 |
| 315 | 25.1 | 361.0 | 0.07 |
| 311 | 14.0 | 260.5 | 0.06 |
| 69 | 9.3 | 140.0 | 0.07 |
| 207 | 30.6 | 199.9 | 0.15 |
| 378 | 29.4 | 347.0 | 0.08 |
| 62 | 14.3 | 145.4 | 0.10 |
| 326 | 39.4 | 137.5 | 0.30 |
| 117 | 17.0 | 292.0 | 0.06 |
| 49 | 23.2 | 514.4 | 0.05 |
| 374 | 36.2 | 244.9 | 0.15 |
| 197 | 24.0 | 610.0 | 0.004 |
| 68 | 10.3 | 535.0 | 0.02 |
| 246 | 38.6 | 192.4 | 0.20 |
| 98 | 17.6 | 135.0 | 0.13 |
| 113 | 10.2 | 685.4 | 0.02 |
| 140 | 21.8 | 127.4 | 0.17 |
| 224 | 8.0 | 224.0 | 0.04 |
| 168 | 11.9 | 80.4 | 0.15 |
| 153 | 28.4 | 496.0 | 0.06 |
| 362 | 22.8 | 158.8 | 0.14 |
| 309 | 28.3 | 182.8 | 0.16 |
| 129 | 26.1 | 705.0 | 0.04 |
| 144 | 13.9 | 103.0 | 0.13 |
| 118 | 30.0 | 168.0 | 0.18 |
| 376 | 14.4 | 81.5 | 0.19 |
| 287 | 32.7 | 98.1 | 0.33 |

TABLE 4

Patients with Low Plasma Level and Normal Urinary Excretion of AC 79

| Patient Test Number | Plasma Level (nMoles/ml) | Urinary Excretion (μMoles/day) | Plasma $\times 10^3$ Urine [24 hr.] |
|---|---|---|---|
| 157 | 15.2 | 63.7 | 0.24 |
| 355 | 16.8 | 62.0 | 0.27 |
| 352 | 11.9 | 55.6 | 0.22 |
| 247 | 10.6 | 57.7 | 0.18 |
| 235 | 34.2 | 57.7 | 0.59 |
| 146 | 14.0 | 59.5 | 0.24 |
| 210 | 21.8 | 66.6 | 0.33 |
| 232 | 12.2 | 52.8 | 0.20 |
| 147 | 11.9 | 44.0 | 0.27 |
| 126 | 7.5 | 71.6 | 0.10 |
| 327 | 24.5 | 48.5 | 0.50 |
| 10 | 20.7 | 48.6 | 0.43 |
| 21 | 8.0 | 53.2 | 0.15 |
| 353 | 6.2 | 61.6 | 0.10 |
| 379 | 24.4 | 60.4 | 0.40 |
| 335 | 27.4 | 58.6 | 0.47 |

TABLE 4-continued

Patients with Low Plasma Level and Normal Urinary Excretion of AC 79

| Patient Test Number | Plasma Level (nMoles/ml) | Urinary Excretion (μMoles/day) | Plasma × 10³ Urine [24 hr.] |
|---|---|---|---|
| 367 | 32.2 | 44.2 | 0.73 |

TABLE 5

Patients with Low, Plasma Level and Low Urinary Excretion of AC 79

| Patient Test Number | Plasma Level (nMoles/ml) | Urinary Excretion (μMoles/day) | Plasma × 10³ Urine [24 hr.] |
|---|---|---|---|
| 170 | 34.5 | 28.8 | 1.20 |
| 251 | 39.5 | 34.8 | 1.13 |
| 356 | 9.8 | 27.6 | 0.35 |
| 258 | 37.4 | 34.0 | 1.10 |
| 159 | 26.3 | 27.3 | 0.96 |
| 104 | 19.4 | 32.2 | 0.60 |
| 193 | 17.0 | 32.4 | 0.52 |
| 209 | 11.7 | 21.3 | 0.55 |
| 142 | 27.9 | 25.9 | 1.08 |
| 34 | 9.6 | 17.6 | 0.55 |
| 206 | 13.6 | 30.9 | 0.44 |
| 200 | 8.5 | 36.0 | 0.23 |

TABLE 6

Patients with Normal Plasma Level and High Urinary Excretion of AC 79

| Patient Test Number | Plasma Level (nMoles/ml) | Urinary Excretion (μMoles/day) | Plasma × 10³ Urine [24 hr.] |
|---|---|---|---|
| 14 | 44.2 | 125.0 | 0.35 |
| 160 | 44.6 | 303.7 | 0.15 |
| 321 | 70.0 | 227.5 | 0.27 |
| 259 | 45.3 | 242.0 | 0.19 |
| 333 | 44.5 | 161.2 | 0.29 |
| 120 | 48.7 | 172.0 | 0.28 |
| 99 | 42.5 | 336.0 | 0.13 |
| 161 | 44.2 | 383.0 | 0.12 |
| 108 | 47.6 | 140.5 | 0.34 |
| 268 | 62.5 | 227.5 | 0.27 |
| 208 | 92.5 | 139.0 | 0.66 |

TABLE 7

Patients with Normal Plasma Level and Normal Urinary Excretion of AC 79

| Patient Test Number | Plasma Level (nMoles/ml) | Urinary Excretion (μMoles/day) | Plasma × 10³ Urine [24 hr.] |
|---|---|---|---|
| 205 | 49.8 | 40.4 | 1.24 |
| 255 | 84.1 | 45.0 | 1.88 |
| 245 | 48.5 | 66.2 | 0.73 |
| 165 | 67.2 | 32.5 | 2.07 |
| 122 | 101.0 | 45.0 | 2.25 |

D. Evaluation of Urinary Antineoplaston Levels in Cancer Patients Undergoing Cancer Chemotherapy Cancer patients frequently excrete a large quantity of AC 63 that ranges from 2 to 280 times the amount present in normal control. The elevation of this component in the urine seems to correlate with cellular death, either of normal cells or necrotic tumor cells. Correspondingly, conventional cytotoxic agents used for cancer chemotherapy often cause elevated excretion of this component. The results presented in Table 8 indicate that the excretion of AC 63 was enhanced 20-fold during the day the patient was given CCNU, cyclophosphamide, and vincristine. The excretion of AC 79 and AC 101 was also greatly elevated. The dramatic increase of AC 63 caused by cytotoxic agents is good evidence linking this component with cellular death. From Applicant's analyses of cancer patients, an elevated level of AC 63 correlates well with advanced malignancy. In addition to the common antineoplaston components evident among normal persons and cancer patients, Applicant's testing procedures provided herein also indicates the presence of unusual components such as AC 35, AC 57, AC 66, AC 76 and AC 93 in cancer patients. These components often disappear as the patients improve following antineoplaston therapy.

TABLE 8

Excretion of Antineoplaston Components Induced by Conventional Cancer Chemotherapeutic Agents

| Antineoplaston Component | Urinary Excretion (μMoles/day) | |
|---|---|---|
| | before Medication | on Medication |
| 10 | 47.5 | 8.5 |
| 26 | 125.0 | 98.0 |
| 35 | 1.3 | 24.5 |
| 48 | 17.1 | 27.1 |
| 57 | 0 | 40.7 |
| 63 | 51.2 | 1080.0 |
| 66 | 0 | 41.5 |
| 79 | 64.5 | 381.0 |
| 85 | 3.0 | 4.4 |
| 93 | 0 | 2.0 |
| 101 | 21.5 | 67.5 |

E. Quantification of Urinary and Plasma Levels of Antineoplastons in Monitoring the Effectiveness of Antineoplaston Therapy Deficiency of plasma antineoplaston components, particularly AC 79, is evidently a significant abnormality associated with a large proportion of cancer patients. Combatting cancer by the correction of this abnormality is the basis of antineoplaston therapy. Several antineoplaston preparations are provided by Applicant and described in his copending U.S. patent applications, Ser. Nos. 279,278 and 330,383, and in related articles referenced heretofore. Of the preparations provided in Applicant's copending patent applications, most of the preparations contain AC 79 as a major constituent.

Cancer patients with a low plasma level of AC 79 usually respond well to antineoplaston therapy. To monitor the effectiveness of antineoplaston therapy, Applicant frequently evaluated the antineoplaston levels in patients undergoing antineoplaston therapy. Specimens were collected six hours after the last injection of antineoplaston preparation to minimize its immediate concentrated influence. Preferably specimens are taken after the administered antineoplaston or other chemotherapeutic agent have returned to steady state level. The typical cases are presented in Table 9.

TABLE 9

Elevation of Plasma Level and Reduction of Urinary Excretion of Antineoplastons Following Antineoplaston Treatment

| | Antineoplaston Component | Patient | | | | | | | | |
|---|---|---|---|---|---|---|---|---|---|---|
| | | MT | | MC | | CL | | HP | | |
| | | Date | | | | | | | | |
| | | 5-28-81 | 7-21-81 | 4-2-81 | 4-23-81 | 4-30-81 | 8-17-81 | 9-24-81 | 7-27-81 | 8-6-81 |
| Plasma Levels (nmoles/ml) | 10 | 0 | 0.9 | 0 | 3.7 | 8.3 | 0 | 0 | 0 | 0.8 |
| | 26 | 20.8 | 37.9 | 13.9 | 6.3 | 27.0 | 0 | 0.7 | 40.7 | 56.2 |
| | 48 | 8.8 | 3.2 | 5.2 | 2.2 | 0.5 | 0 | 0.7 | 0.3 | 3.2 |
| | 63 | 25.6 | 8.0 | 12.5 | 1.5 | 7.2 | 0 | 12.7 | 13.6 | 15.7 |
| | 79 | 21.8 | 93.6 | 17.0 | 45.2 | 43.5 | 4.6 | 50.8 | 25.1 | 101.9 |
| | 101 | 23.8 | 20.6 | 23.1 | 5.1 | 3.9 | 0.5 | 10.3 | 12.9 | 7.4 |
| Urinary Excretion (μmoles/day) | 10 | 0 | 13.2 | 21.4 | 27.1 | 1.6 | 14.1 | 8.4 | 16.6 | 17.5 |
| | 26 | 79.5 | 7.2 | 31.7 | 7.0 | 14.4 | 4.8 | 0 | 212.5 | 24.3 |
| | 48 | 9.2 | 15.2 | 17.6 | 118.0 | 27.6 | 24.1 | 16.6 | 25.5 | 22.0 |
| | 63 | 21.3 | 22.5 | 29.4 | 390.0 | 75.0 | 21.1 | 13.3 | 37.8 | 63.0 |
| | 79 | 66.6 | 48.9 | 292.0 | 108.0 | 52.5 | 138.5 | 57.3 | 361.0 | 129.1 |
| | 101 | 17.7 | 20.1 | 65.3 | 20.4 | 10.4 | 19.5 | 7.9 | 68.4 | 84.2 |
| Plasma/Urine Ratios | 10 | 0 | 0.06 | 0 | 0.13 | 5.18 | 0 | 0 | 0 | 0.04 |
| | 26 | 0.26 | 5.26 | 0.43 | 0.90 | 1.87 | 0 | 0 | 0.19 | 2.31 |
| | 48 | 0.95 | 0.21 | 0.29 | 0.01 | 0.01 | 0 | 0.04 | 0.01 | 0.15 |
| | 63 | 1.20 | 0.35 | 0.42 | 0.003 | 0.09 | 0 | 0.95 | 0.35 | 0.25 |
| | 79 | 0.32 | 1.91 | 0.05 | 0.41 | 0.82 | 0.03 | 0.88 | 0.06 | 0.79 |
| | 101 | 1.34 | 1.02 | 0.35 | 0.25 | 0.37 | 0.02 | 1.30 | 0.18 | 0.09 |

The patients show elevation of the plasma level of AC 79, at the same time urinary excretion of antineoplaston components, particularly AC 79, is promptly reduced to the levels of normal control. It is, however, not unusual that urinary excretion of AC 48 and AC 63 during the initial period of therapy goes up and comes back down, as illustrated by the MC results in Table 9. The increased excretion of AC 48 and AC 63 during the initial period of therapy probably reflects the massive destruction of tumor cells. Patients showing early responses, as those listed in Table 9, are considered to be responding favorably to antineoplaston therapy. Such patients will eventually enter into remission as the antineoplaston levels approach those of normal control. Table 10 presents four patients in remission having antineoplaston levels very similar to a normal control.

TABLE 10

Antineoplaston Levels for Patients in Remission

| | Antineoplaston Component | Test Number | | | |
|---|---|---|---|---|---|
| | | 97 | 236 | 649 | 127 |
| Plasma Levels (nMoles/ml) | 10 | 0 | 55.7 | 0 | 0.5 |
| | 26 | 8.5 | 35.0 | 1.4 | 0.2 |
| | 48 | 5.3 | 1.2 | 0 | 0.5 |
| | 63 | 9.8 | 4.2 | 22.0 | 1.4 |
| | 79 | 64.4 | 197.4 | 29.6 | 125.0 |
| | 101 | 3.2 | 13.7 | 3.9 | 11.2 |
| Urinary Excretion (μMoles/day) | 10 | 1.4 | 14.1 | 9.3 | 123.0 |
| | 26 | 0 | 6.6 | 1.2 | 112.0 |
| | 48 | 2.7 | 4.1 | 17.4 | 21.3 |
| | 63 | 5.3 | 17.7 | 37.1 | 27.0 |
| | 79 | 68.0 | 23.1 | 42.8 | 54.5 |
| | 101 | 4.8 | 2.3 | 36.1 | 31.0 |
| Plasma/ Urine Ratios | 10 | 0 | 3.95 | 0 | 0.004 |
| | 26 | ∞ | 5.30 | 1.17 | 0.002 |
| | 48 | 1.96 | 0.29 | 0 | 0.02 |
| | 63 | 1.85 | 0.24 | 0.59 | 0.05 |
| | 79 | 0.95 | 8.54 | 0.69 | 2.30 |
| | 101 | 0.67 | 5.95 | 0.10 | 0.37 |

The foregoing description of the invention has been directed to particular examples relating to quantitative evaluation of small-sized peptide antineoplastons from human urine and plasma for purposes of explanation and illustration. It is to be understood, however, that modifications and changes in the methods of analysis, the process for fractionating antineoplastons, and the antineoplaston fraction selected for evaluation can be made in the implementation and utilization of the present invention to aid in the diagnosis of cancer and monitor antineoplaston therapy without departing from the scope of the invention defined in the claims. For example, it is contemplated that antineoplastons other than the small-sized antineoplastons described herein provide an indicator to aid in the diagnosis of cancer and to monitor the progress of antineoplaston therapy. Furthermore, it will be appreciated by practioners in the art that antineoplaston levels can be evaluated from physiological sources other than urine or plasma, such as saliva, organ biopsy tissue or whole blood samples. It is to be understood that Applicant directed his evaluation efforts to urine and plasma based on convenience and bioanalytical sensitivity capabilities of instrumentation utilized in quantitating antineoplaston levels.

What is claimed is:

1. A method of diagnosing neoplastic disease in a subject suspected of having neoplastic disease comprising:
   providing a test sample of physiological tissue or fluid obtained from the subject;
   quantitatively determining the level of antineoplaston within the test sample;
   comparing the level of antineoplaston of the test sample to a standard antineoplaston level assessed from like tissue or fluid samples obtained from normal subjects unaffected by neoplastic disease, a significant difference in the two levels being indicative of neoplastic disease.

2. The method in accordance with claim 1 wherein the test sample is urine.

3. The method in accordance with claim 1 wherein the test sample is whole blood, plasma or serum.

4. The method in accordance with claim 1 wherein the level of antineoplaston is determined by chromatographic fractionation means.

5. The method in accordance with claim 1 wherein the antineoplaston quantitated includes peptides.

6. The method in accordance with claim 1 wherein the antineoplaston quantitated includes small-sized peptides, having less than ten amino acid residues.

7. The method in accordance with claim 1 wherein the antineoplaston quantitated includes 3-[N-phenylacetylaminopiperidine]-2, 6-dion.

8. The method in accordance with claim 1 wherein the antineoplaston quantitated is an amino acid derivative.

9. A method of diagnosing neoplastic disease in a subject suspected of having neoplastic disease comprising:
providing a test sample of physiological tissue or fluid obtained from said subjects;
extracting from said test sample antineoplaston;
fractionating the antineoplaston extract to obtain a plurality of fractions;
selecting for further evaluation a fraction containing an antineoplaston substance;
quantitatively determining the level of antineoplaston present within the selected fraction; and
comparing the level of antineoplaston of the selected fraction to a standard antineoplaston level assessed from like tissue or fluid samples obtained from normal subjects unaffected by neoplastic disease, a significant difference in the two levels being indicative of neoplastic disease.

10. The method in accordance with claim 9 wherein the test sample provided in urine.

11. The method in accordance with claim 9 wherein the test sample provided is whole blood, plasma or serum.

12. The method in accordance with claim 9 wherein the fractionation is accomplished by chromatographic fractionation means.

13. The method in accordance with claim 9 wherein the antineoplaston extracted from the test sample includes peptides.

14. The method in accordance with claim 9 wherein the antineoplaston extracted from the test sample includes small-sized peptides having less than ten amino acid residues, or amino acid derivatives.

15. The method in accordance with claim 9 wherein the fraction selected contains 3-[N-phenylacetylaminopiperidine]-2, 6-dion.

16. The method in accordance with claim 9 wherein the fraction selected contains an amino acid derivative.

17. A method for diagnosing neoplastic disease in a subject suspected of having neoplastic disease comprising:
providing a first test sample of physiological tissue or fluid obtained from the subject:
providing a second test sample of physiological tissue or fluid obtained from the subject, the second test sample being of a different physiological origin than the first test sample;
quantitatively determining the level of antineoplaston within each test sample;
evaluating the ratio of antineoplaston levels between the first and second test sample; and
comparing the ratio of test samples to a standard antineoplaston ratio associated with like tissue or fluid samples obtained from normal subjects unaffected by neoplastic disease, a significant difference in ratios being indicative of neoplastic disease.

18. The method in accordance with claim 17 wherein the first test sample is whole blood, plasma or serum and the second test sample is urine.

19. The method in accordance with claim 17 wherein the antineoplaston level is determined by chromatographic fractionation means.

20. The method in accordance with claim 17 wherein the antineoplaston quantitated includes peptides.

21. The method in accordance with claim 17 wherein the antineoplaston quantitated includes small-sized peptides having less than ten amino acid residues.

22. The method in accordance with claim 17 wherein the antineoplaston quantitated includes 3-[N-phenylacetylaminopiperidine]-2, 6-dion.

23. The method in accordance with claim 17 wherein the antineoplaston quantitated is an amino acid derivative.

24. A method of assessing the progress of antineoplastic therapy in a subject diagnosed with neoplastic disease, comprising:
providing a test sample of physiological tissue or fluid obtained from the subject;
quantitatively determining the level of antineoplaston within the sample;
comparing the level of antineoplaston of the test sample to a standard antineoplaston level assessed from like tissue or fluid samples taken from normal subjects unaffected by neoplastic disease, levels substantially the same being indicative of the remission of neoplastic disease.

25. The method in accordance with claim 24 wherein the test sample is urine.

26. The method in accordance with claim 24 wherein the test sample is whole blood, plasma or serum.

27. The method in accordance with claim 24 wherein the test sample provided for antineoplaston quantification is obtained from the subject after steady state level of administered chemotherapeutic agent is retained.

28. The method in accordance with claim 24 wherein the level of antineoplaston is determined by chromatographic fractionation means.

29. The method in accordance with claim 24 wherein the antineoplaston quantitated includes peptides.

30. The method in accordance with claim 24 wherein the antineoplaston quantitated includes small-sized peptides, having less than ten amino acid residues.

31. The method in accordance with claim 24 wherein the antineoplaston quantitated includes 3-[N-phenylacetylaminopiperidine]-2, 6-dion.

32. The method in accordance with claim 24 wherein the antineoplaston quantitated includes amino acid derivatives.

33. A method of assessing the progress of antineoplastic therapy in a subject diagnosed with neoplastic disease, comprising:
providing a test sample of physiological tissue or fluid obtained from said subjects;
extracting from said test sample antineoplaston;
fractionating the antineoplaston extract to obtain a plurality of fractions;
selecting for further evaluation a fraction containing an antineoplaston substance;
quantitatively determining the level of antineoplaston present within the selected fraction; and
comparing the level of antineoplaston of the selected fraction to a standard antineoplaston level assessed from like tissue or fluid samples obtained from normal subjects unaffected by neoplastic disease, levels substantially the same being indicative of the remission of neoplastic disease.

34. The method in accordance with claim 33 wherein the test sample provided is urine.

35. The method in accordance with claim 33 wherein the test sample provided in whole blood, plasma or serum.

36. The method in accordance with claim 33 wherein the fractionation is accomplished by chromatographic fractionation means.

37. The method in accordance with claim 33 wherein the antineoplaston extracted from the test sample includes peptides.

38. The method in accordance with claim 33 wherein the antineoplaston extracted from the test sample includes small-sized peptides having less than ten amino acid residues, or amino acid derivatives.

39. The method in accordance with claim 33 wherein the fraction selected contains 3-[N-phenylacetylaminopiperidine]-2, 6-dion.

40. The method in accordance with claim 33 wherein the fraction selected contains amino acid derivatives.

41. A method of assessing the progress of antineoplastic therapy in a subject diagnosed with neoplastic disease, comprising:

providing a first test sample of physiological tissue or fluid obtained from the subject;

providing a second test sample of physiological tissue or fluid obtained from the subject, the second test sample being of a different physiological origin than the first test sample;

quantitatively determining the level of antineoplaston within each test sample;

evaluating the ratio of antineoplaston levels between the first and second test sample; and comparing the ratio of test samples to a standard antineoplaston ratio associated with like tissue or fluid samples obtained from normal subjects unaffected by neoplastic disease, ratios substantially the same being indicative of the remission of neoplastic disease.

42. The method in accordance with claim 41 wherein the first test sample is whole blood, serum or plasma and the second test sample is urine.

43. The method in accordance with claim 41 wherein the antineoplaston level is determined by chromatographic fractionation means.

44. The method in accordance with claim 41 wherein the antineoplaston quantitated includes peptides.

45. The method in accordance with claim 41 wherein the antineoplaston quantitated includes small-sized peptides, having less than ten amino acid residues.

46. The method in accordance with claim 41 wherein the antineoplaston quantitated includes 3-[N-phenylacetylaminopiperidine]-2, 6-dion.

47. The method in accordance with claim 41 wherein the antineoplaston quantitated includes an amino acid derivative.

* * * * *